United States Patent [19]

Falco

[11] Patent Number: 5,799,658
[45] Date of Patent: Sep. 1, 1998

[54] HEARING PROTECTIVE DEVICE COMPRISING A FOAM AND A POROUS COMPONENT AND METHOD OF MANUFACTURE THEREOF

[75] Inventor: Robert N. Falco, Indianapolis, Ind.

[73] Assignee: Cabot Safety Intermediate Corporation, Southbridge, Mass.

[21] Appl. No.: 698,398

[22] Filed: Aug. 15, 1996

[51] Int. Cl.$^6$ .................................................. A61F 11/00
[52] U.S. Cl. .................. 128/864; 128/865; 181/129
[58] Field of Search ................ 128/846, 864–868; 2/2, 208, 209; 181/129, 130

[56] References Cited

U.S. PATENT DOCUMENTS

| Re. 29,487 | 12/1977 | Gardner, Jr. . | |
|---|---|---|---|
| 2,538,339 | 1/1951 | Thomas | 128/864 |
| 2,672,863 | 3/1954 | Leight | 128/867 |
| 4,314,553 | 2/1982 | Westerdy | 128/864 |
| 4,461,290 | 7/1984 | Gardner, Jr. et al. . | |
| 4,671,265 | 6/1987 | Andersson . | |
| 4,774,938 | 10/1988 | Leight | 128/864 |
| 5,071,331 | 12/1991 | Falco . | |
| 5,188,123 | 2/1993 | Gardner, Jr. . | |
| 5,203,352 | 4/1993 | Gardner, Jr. . | |
| 5,420,381 | 5/1995 | Gardner, Jr. et al. . | |

OTHER PUBLICATIONS

Interflo Product Applications Brochure.

*Primary Examiner*—Michael A. Brown
*Attorney, Agent, or Firm*—Fishman, Dionne, Cantor & Colburn

[57] ABSTRACT

An acoustical hearing device is presented, including a foam and at least one porous component which is mechanically bonded to the foam. The mechanical bonding of the porous component arises during manufacture, wherein the porous component is placed into a mold cavity as an insert and a foam is formed within the mold so as to allow controlled penetration of the porous component during foaming. Importantly, entrapped air in the closed cavity may pass through the porous component during manufacture, thereby allowing the porous component to act as a mold vent. A method of manufacture of the hearing protective device of the present invention is also presented.

34 Claims, 4 Drawing Sheets

HEARING PROTECTIVE DEVICE COMPRISING A FOAM AND A POROUS COMPONENT AND METHOD OF MANUFACTURE THEREOF

BACKGROUND OF THE INVENTION

1. Field of the Invention

The present invention relates generally to acoustical hearing protective devices, and more particularly to hearing protective devices comprising a foam and at least one mechanically bonded porous component which may also serve as a vent during the manufacturing process.

2. Brief Description of the Prior Art

The use of hearing protection and noise attenuating devices are well known, and various types of devices are available for this purpose. Such devices include, but are not limited to, earmuffs, semi-aural devices, and earplugs. Foam components are well-known for use with these devices, providing both sound attenuation and enhanced comfort for the wearer.

Most earmuffs are made up of a band section, a cup section, and a cushion section. The band section extends between the pair of muffs, and holds the muffs snugly against the head of the wearer. The cup section is typically filled with foam material, and in this combination of cup and foam is where the sound attenuation takes place. An exemplary earmuff cushion is described U.S. Pat. No. 5,420,381 to Gardner, Jr. et al. Earmuffs are advantageous for intermittent uses where continuous insertion and removal of earplugs would be annoying or impractical. Earmuffs also tend to deliver higher infield noise protection in many high-frequency noise environments. However, earmuffs may comprise a multiplicity of parts, resulting in increased manufacturing costs and assembly time.

A typical semi-aural hearing protector assembly generally comprises a resilient U-shaped band with holders at either end, and a pair of inwardly directed ear protectors ("pods") that are detachably mounted to the holders. Semi-aural hearing protectors fall generally into three categories, including protectors that cap the entrance to the ear canal; protectors which enter the ear canal and seal the ear canal prior to the bend in the ear canal (usually referred to simply as semi-aural devices); and protectors that enter the ear canal and take the bend in the ear canal (sometimes referred to as banded earplugs). As used herein, "semi-aural hearing protectors" refers generally to any hearing protector falling into one of the three categories described above.

Attenuation for semi-aural hearing protectors generally increases as entry into the ear canal increases. However, comfort is inverse to attenuation, with comfort increasing as entry into the ear canal decreases. Thus there is apparently no commercially viable banded earplugs (i.e., semi-aural hearing protectors designed to take the bend of the ear canal) available which are comfortable enough for widespread use. Semi-aural hearing protectors thus protect similarly to earplugs, but usually to a lesser level. Semi-aural hearing protectors which enter the ear canal to a greater degree offer better protection but are somewhat less comfortable than those which simply cap the ear. Products which cap the ear have some of the attributes of both earplugs and earmuffs. Typically, they are used for intermittent noise exposures where lighter weight and improved low frequency attenuation are desirable. U.S. Pat. No. 4,461,290 to Gardner, Jr. et al. discloses a semi-aural device incorporating a foam component. U.S. Pat. No. 4,671,265 to Andersson also discloses a semi-aural device.

Earplugs are generally preferred for continuous use over longer periods of time. Slow recovery foam earplugs such as those disclosed in U.S. Reissue. No. 29,487 are not only comfortable, but have also been shown to deliver high in-field noise protection at all frequencies. U.S. Pat. No. 5,203,352 to Gardner, Jr. also discloses a hearing protective earplug comprising a polymeric foam.

With respect to all three types of devices, the sound-attenuating (acoustical) component has been made both of flexible, rubber-like materials, and of foam. For earplugs and semi-aural devices, the rubber-like materials are advantageous in allowing direct insertion into the wearer's ear, but are sometimes uncomfortable over long periods of use. Foam earplugs and pods provide enhanced comfort, but require "rolling down" before insertion. In addition, manufacture of foam components requires the presence of a vent in the mold for entrapped gases to escape, which often results in foam overflowing the vent ("flash"). This flash is wasteful, and must be cleaned off the molds after each molding. Cleaning the molds can be a long, tedious procedure which adds significantly to manufacturing time.

A foam earplug or pod with a stem insert can provide both the ease of insertion of rubber-like earplugs, with the comfort of foam earplugs and pods. In fact, a number of patents have been directed to earplugs having tips or flanges with a relatively stiff stem used to insert and remove the earplug. One especially useful earplug, shown in FIG. 1, is described in U.S. Pat. No. 5,188,123 to Gardner, herein incorporated by reference. This earplug 2 comprises a circular or ovoid resilient polymeric foam body 4 having a rounded nose end 6. An elongate stem 8 is axially embedded in main body element 4 and extends rearwardly and axially therefrom. The earplug may be used in a push-in or roll-down insertion mode.

While suitable for certain purposes, this prior art earplug requires an additional manufacturing step to secure the stem in the foam body, i.e., a gluing step. Furthermore, the bond is sometimes not as permanent as is desirable. In addition, if the stem is too hard it may be considered unsafe to the user, the general concern being that potential injury could result should the hearing protector become impacted. On the other hand, if the stem is too soft, it tends to buckle upon insertion, limiting the fit of the earplug and reducing the potential usefulness of the stem.

One attempted solution has been to provide an insertion tool, consisting of a stiff tube that fits over the soft stem. However, the use of an additional part increases the cost of manufacture and may be inconvenient for the user. Another attempted solution has been to use a relatively stiff material, but reduce the diameter of the stem. However, this solution results in decreased comfort for the wearer, apparently due to the increased pressure that results from use of a smaller diameter stem.

Accordingly, there remains a need for a stemmed foam earplug and pod that is safe for the wearer, yet convenient and comfortable to use, and which does not requires a separate gluing step to adhere the stem or other porous part. There also remains a need for a ventless manufacturing process which does not require excessive cleaning of the mold after each use.

BRIEF DESCRIPTION OF THE DRAWINGS

Referring now to the drawings wherein like elements are numbered alike in the several FIGURES.

SUMMARY OF THE INVENTION

Figure 1:
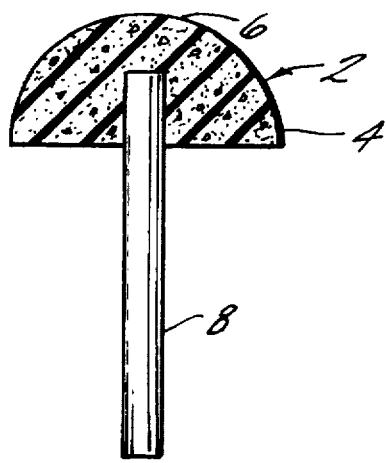
FIG. 1 is a prior art earplug.

The above-discussed and other problems and deficiencies of the prior art are overcome or alleviated by the foam hearing protective devices and method of manufacture of the present invention, comprising a foam and at least one porous component mechanically bonded to the foam during manufacture by controlled penetration of the porous component by the foam. Importantly, the porous component may also act as a mold vent during the manufacturing process.

In a preferred embodiment of the present invention, an earplug or semi-aural device comprises a foam component mechanically bonded to a porous insert having a handle portion and an embedded portion. "Embedded portion" refers here to that part of the porous insert which is surrounded by, and mechanically bonded to, the foam component. During manufacture, the porous component is placed in a mold and a foam is formed within the mold such that foam penetrates a portion of the porous component, thereby forming a mechanical bond between the foam and the embedded portion of the porous component. Importantly, entrapped air within the mold may also pass through or into the porous component such that the porous component acts as a mold vent.

In an especially preferred embodiment, the respective handles of two earplugs are each bonded to the respective ends of a stretchable cord. The bonding of the handles to the cord ends may occur under thermal or ultrasonic conditions, wherein the cord material penetrates into the pores of the handle portion, thereby forming a mechanical bond. Thus, a strong bond without the use of adhesives is possible even if the handle and cord materials are dissimilar, due to penetration of the cord material into the stem upon thermal or ultrasonic bonding.

In yet another preferred embodiment of the earplug or semi-aural device according to the present invention, the porous component comprises a less stiff portion and a stiffer portion, the portion embedded in the earplug toward the tip being less stiff than the portion outside the earplug used as a handle. The variable stiffness may be achieved by reducing the diameter of the cross-section of the stem within the earplug such that the embedded portion toward the tip is of smaller diameter than the handle portion. Alternatively, the variable stiffness may be achieved by varying the density of the stem, with the handle portion being more dense than the embedded portion toward the tip. Preferably, both reduced cross section and variable density are used simultaneously to achieve the desired utility and comfort.

In still another embodiment of the present invention, an earplug or pod comprises a foam and a non-porous stem having a handle portion and an embedded portion, the stem also being of variable stiffness. The variable stiffness may be achieved by varying the diameter of the cross-section of the stem, by varying the density of the stem, by varying the hardness of the stem, or by varying the material of which the stem is made. Preferably, both reduced cross section and variable density are used simultaneously to achieve the desired utility and comfort.

In the preferred method of the present invention, a porous insert is placed into the cavity of a mold, and a foam is then introduced. As the foam rises, it interpenetrates at least some of the pores in the insert, thereby forming a mechanical bond between the insert and the finished foam. This process eliminates the need for an additional gluing step during manufacture. The porous insert may also act as a mold vent during the foaming process to remove trapped gas from within the mold. Because no or little foam escapes from the vent, this process reduces waste, scrap, and time required for mold cleaning.

The above-discussed and other features and advantages of the present invention will be appreciated and understood by those skilled in the art from the following detailed description and drawings.

DESCRIPTION OF THE PREFERRED EMBODIMENT

The acoustical device and method of manufacture of the present invention comprises a foam and at least one porous component mechanically bonded to the foam during manufacture by controlled penetration of the porous component by the foam. Importantly, the porous component may also act as a mold vent during the manufacturing process.

Figure 2:
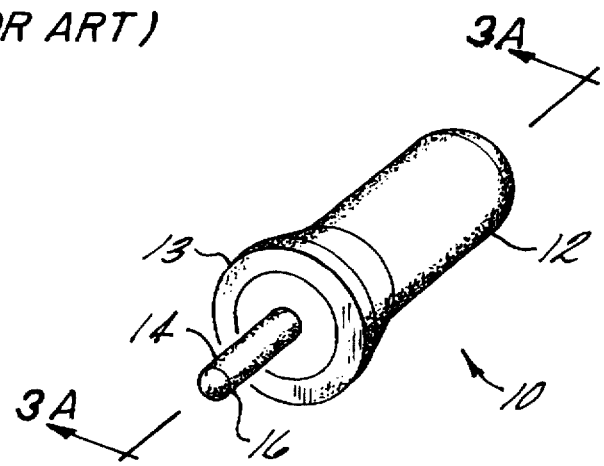
FIG. 2 is an elevational view of an earplug or pod according to the present invention.
Figure 3A:
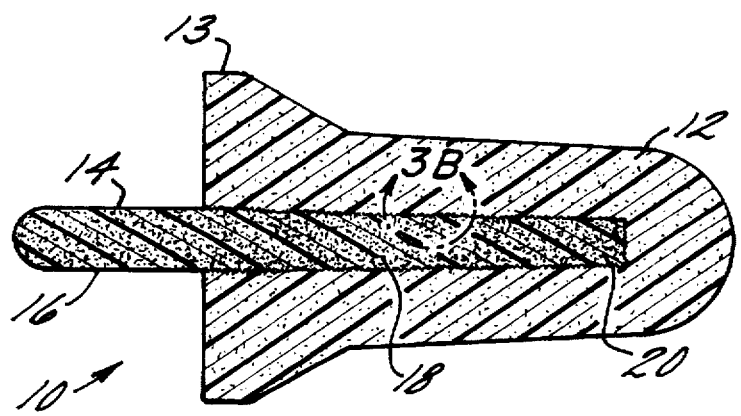
FIG. 3A is a cross-sectional view through FIG. 2 of an earplug or pod according to the present invention.
Figure 3B:
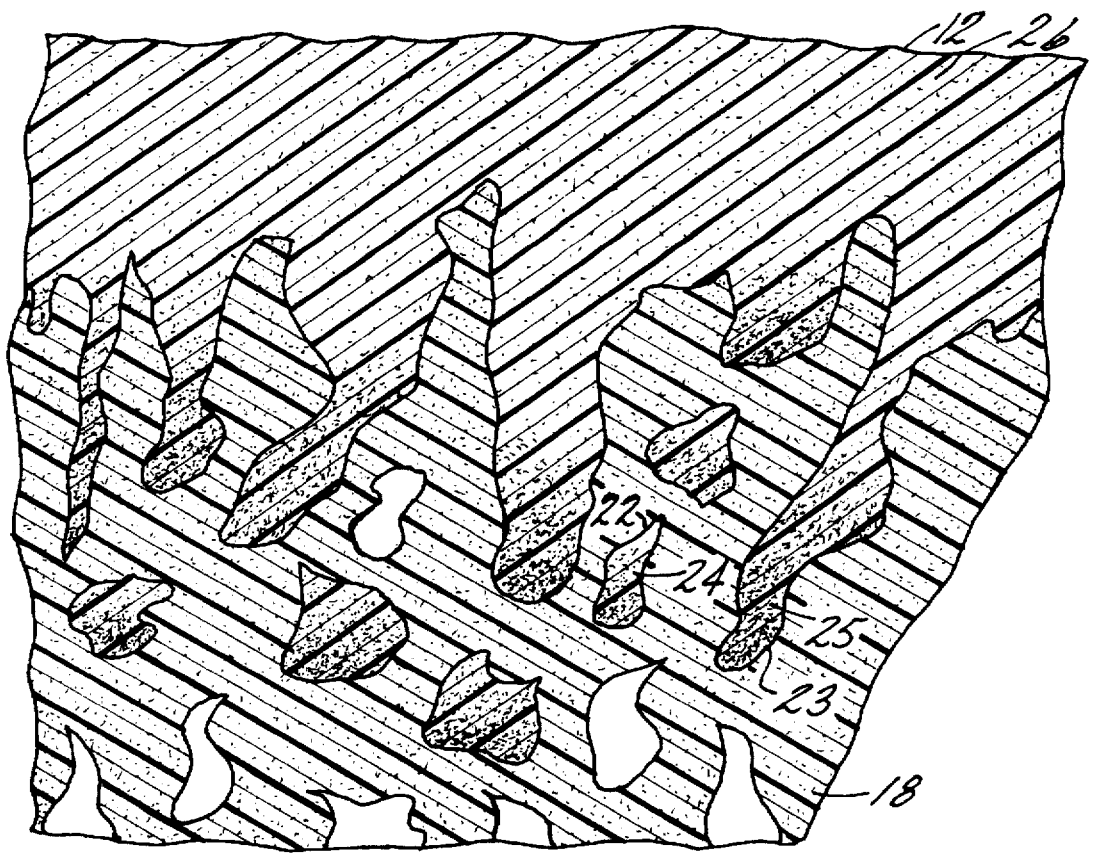
FIG. 3B is an enlarged detail view taken from FIG. 3A.

Referring now to FIGS. 2 and 3, in a preferred embodiment of the present invention the earplug or semi-aural device pod 10 comprises a foam 12 mechanically bonded to a porous component 14 having a handle portion 16 and an embedded portion 18 with a tip 20. "Embedded portion" refers here to that part of the porous insert which is surrounded by, and mechanically bonded to, the foam component. The earplug may be of any configuration, such as circular or ovoid, with the preferred configuration having a flange 13. During manufacture, porous component 14 is placed in a mold and a foam is formed within the mold such that foam penetrates the embedded portion 18 of porous component 14, thereby forming a mechanical bond between the foam and the porous component. This mechanical bond is shown in greater detail in FIG. 3B, where foam 12 has penetrated various pores 22, 23 in porous component 14. It is likely that foam 24, 25 which has interpenetrated these pores is denser than the foam 26 surrounding porous component 14.

Importantly, entrapped air within the mold may also pass through the porous portion prior to the foam forming a mechanical bond with the stem, such that porous component 14 acts as a mold vent. Porous component 14 also serves to block the vent in the mold, preventing overflow of foam during manufacture, thus reducing waste and saving manufacturing time.

Preferably, the porous component is used as a stem for an earplug or semi-aural device. As such, the porous component must be rigid enough to aid insertion into the wearer's ear, yet soft and pliable enough to be comfortable and safe for the wearer. The component should also be stiff enough to allow the wearer to roll down the earplug portion before insertion if desired. While the porous part may be of uniform stiffness, preferably the stiffness varies such that the handle portion 16 is stiffer than the embedded portion 18 toward the tip 20. This varying stiffness may be achieved by varying the density of the handle portion and the embedded portion, with the handle portion being of greater density than the embedded portion toward the tip. Alternatively, as shown in FIG. 3A, the stiffness may be achieved by varying the diameter of the cross-section of the handle portion 16 and the embedded portion 18, with the diameter of the cross-section of the handle portion 16 being greater than the diameter of the cross-section of the embedded portion toward the tip. Preferably, both variable density and variable cross-sectional diameters are used to achieve the greatest utility and comfort for the wearer.

Narrowing the diameter of the cross-section of the tip of the embedded portion had not been possible previously due to the fact that the stem was required to be glued to the foam. An adequate bond could only be formed by gluing a larger area of stem into the foam, and the adhesive itself increases the effective stem cross-section. The present invention allows formation of a stronger mechanical bond, even using reduced stem surface area.

The porous material is selected so as to be of adequate strength and bendability for use as an earplug stem or other hearing protective device part. The porosity is selected in conjunction with the viscosity of the foaming medium such that controlled penetration of the embedded portion is obtained during foaming. Preferably, the porosity is also selected so as to allow entrapped air in the closed mold to pass through the porous part, thereby venting the mold during manufacture.

Thus, the porous material is preferably a polymer or combination of polymers in the form of particles of one or more size ranges bonded in such a way as to leave voids or pores within the material. The pores may be of varying sizes. Preferably, the pore volume is in the range from about ten percent to about ninety percent of the total volume, with the most preferred pore volume being in the range from about thirty to about sixty percent of the total volume. A particularly preferred porous component is Swab-002 made from INTERFLO®, available from Interflo Technologies, Brooklyn, N.Y. While porous plastics are preferred for use with the present invention, other porous materials may also be suitable.

In yet another embodiment of the present invention, the respective porous stem of two earplugs may be each bonded to one end of a cord in a second step by push-in methods or by other mechanical bonding methods known in the art to form a corded set of earplugs. Alternatively, the cord may be attached through a preformed hole in the porous stem.

Figure 7:
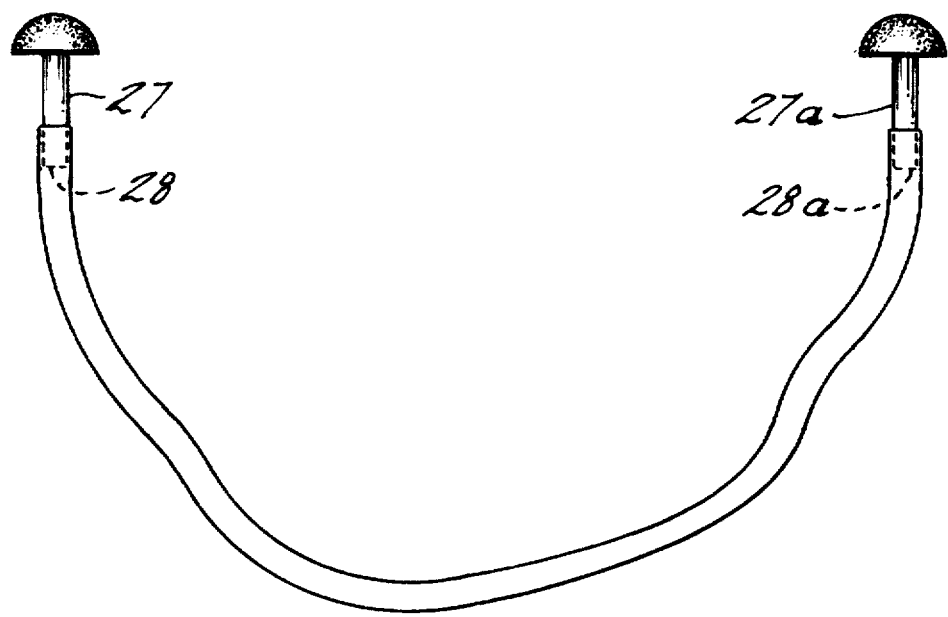
FIG. 7 is a perspective view of a set of corded earplugs according to the present invention.

In an especially preferred embodiment, the respective porous stems of two earplugs are each bonded to the respective ends of a cord as shown in FIG. 7. The bonding of the handles 27, 27a to cord ends 28, 28a may occur under thermal or ultrasonic conditions, wherein the cord material penetrates into the pores of the handle portion, thereby forming a mechanical bond similar to that described above and shown in FIG. 3B. Thus, a strong bond without the use of adhesives is possible even if the handle and cord materials are dissimilar, due to penetration of the cord material into the stem upon thermal or ultrasonic bonding.

As described above, the porous component is subsequently used as a stem to aid insertion of an earplug. However, the present invention also contemplates that the porous component may subsequently be used as, for example, tabs, insert holders, or embedded filters. Such embedded filters could be acoustical, or for air or water vapor. Foam parts containing porous components for other types of hearing protectors, for example earmuffs and semi-aural devices, are also within the scope of this invention.

Figure 8:
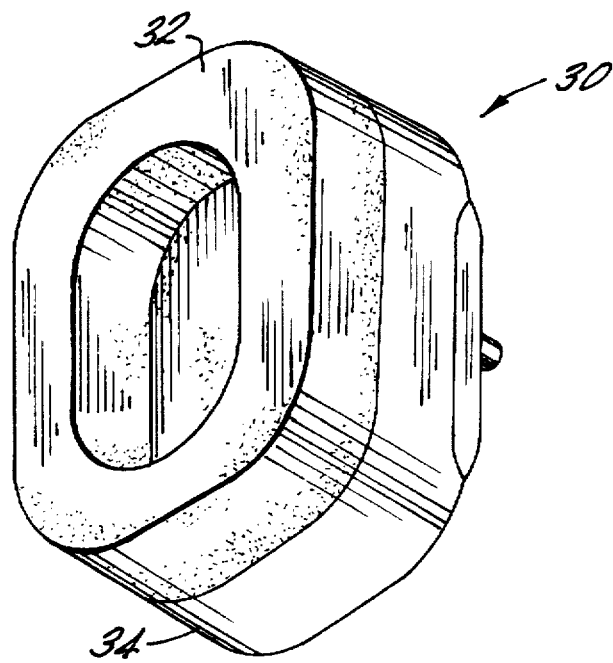
FIG. 8 is a perspective view of a foam component and sealplate according to the present invention.
Figure 9:
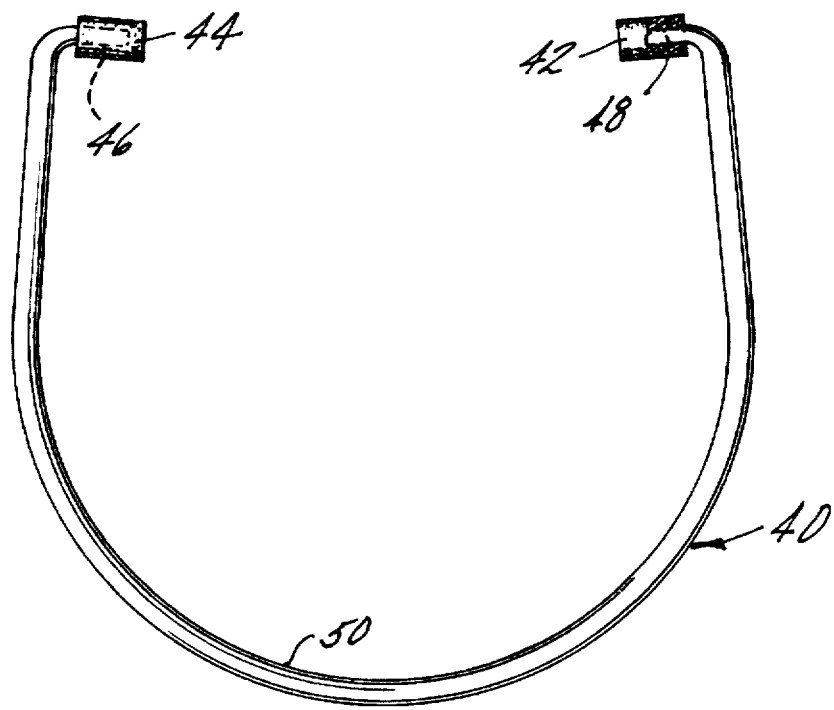
FIG. 9 is a perspective view of foam component and porous headband for a semi-aural device according to the present invention.

With respect to earmuffs, the porous component may include the cushion sealplate or a portion thereof. Thus, as shown for earmuff part 30 in FIG. 8, foam component 32 is at least partially mechanically bonded to sealplate 34 by interpenetration of the foam into the pores of porous sealplate 34. With respect to semi-aural devices, the porous component may include a headband component. Thus, as shown for semi-aural device 40 in FIG. 9, foam component 42, 44 is each at least partially mechanically bonded to a respective end 46,48 of porous headband 50 by interpenetration of the foam into pores of ends 46,48, similarly to the mechanical bonding described above and shown in FIG. 3B.

Although a porous stem is preferred for the practice of the method of the present invention, earplugs and pods for semi-aural devices with stems of variable-stiffness stems made of other suitable non-porous materials are also within the scope of the present invention. Variable stiffness may result from a variation in the diameter of the cross-section of the stem as shown in FIG. 3A, a variation in the density of the stem, a variation in the material used to construct the stem, a variation in the hardness of the stem, or a combination of the preceding characteristics. Suitable materials for stems include, but are not limited to, those known in the art such as polyalkanes, polyvinylcarbonate, polypropylene, polyethylene, polyacrylates, fluoroelastomers, copolymers or multipolymers of the above, ethylene vinyl acetate, and thermoplastic elastomers, including various types of linear, diblock, triblock, and radial polymers of materials such as styrene-butadiene, isoprene-styrene, styrene-ethylene propylene and the like, and blends of the aforementioned with other materials, including metal powders. Preferred materials include polyethylene, polypropylene, ethylene-vinyl acetate, and thermoplastic elastomers, such as KRATON™ thermoplastic rubbers. Suitable materials for non-porous stems include, but are not limited to, those known in the art such as those listed above, wherein glue or adhesive may be required to maintain the foam onto the stem.

Suitable foams for use with the present invention include those self-rising foams suitable for use with foam earplugs or other foam components for hearing protective devices, such as earmuffs. Such foams include soft, pliable self-rising foams with instant recovery. Other foams are self-rising polyurethane or acrylic blend foams with slow recovery. One suitable foam is described in U.S. Pat. No. 5,203,352 to Gardner, herein incorporated by reference. The earplug described therein is comprised of a part slow recovery polymer and a part faster recovery polymer. Another suitable foam is described in U.S. Pat. No. 5,420,381 to Gardner, herein incorporated by reference.

In the method of manufacture of the present invention, a porous plastic component is placed into the cavity of an earplug mold. Foam or a foamable mixture is introduced into the mold, and caused to rise. Rising may be accomplished by any suitable means, for example by using a self-rising foam, or by heating the mold. As the foam rises, it interpenetrates into the pores of the porous component, thereby forming a mechanical bond between the porous component and the finished foam. This method is particularly advantageous in that it provides a safe, useful earplug or semi-aural pod easily and efficiently, without the necessity of an additional bonding step. It has previously been very difficult to form a satisfactory bond between a stem and a foam. Furthermore, the bond formed according to the present invention is very strong, resulting in a better product.

Additionally, this method allows bonding of dissimilar materials such as polyurethane foam to porous polyethylene components. This is particularly remarkable in that polyethylene is ordinarily used as a surface release material for polyurethane foams. With this method, however, a strong mechanical bond is formed by the penetration of polyurethane into the pores within the embedded portion of the stem or other porous component.

Importantly, the porous component may also act as a mold vent during the manufacturing process, by providing a means for gas trapped in the mold to escape. While it is anticipated that gas may be vented through the porous part into the atmosphere, it is not necessary. It may be advantageous to keep the mold a completely closed system, and have the gas vented into the porous part, thereby building pressure in the porous part. This pressure is then released upon removal of the mold top.

Figure 4:
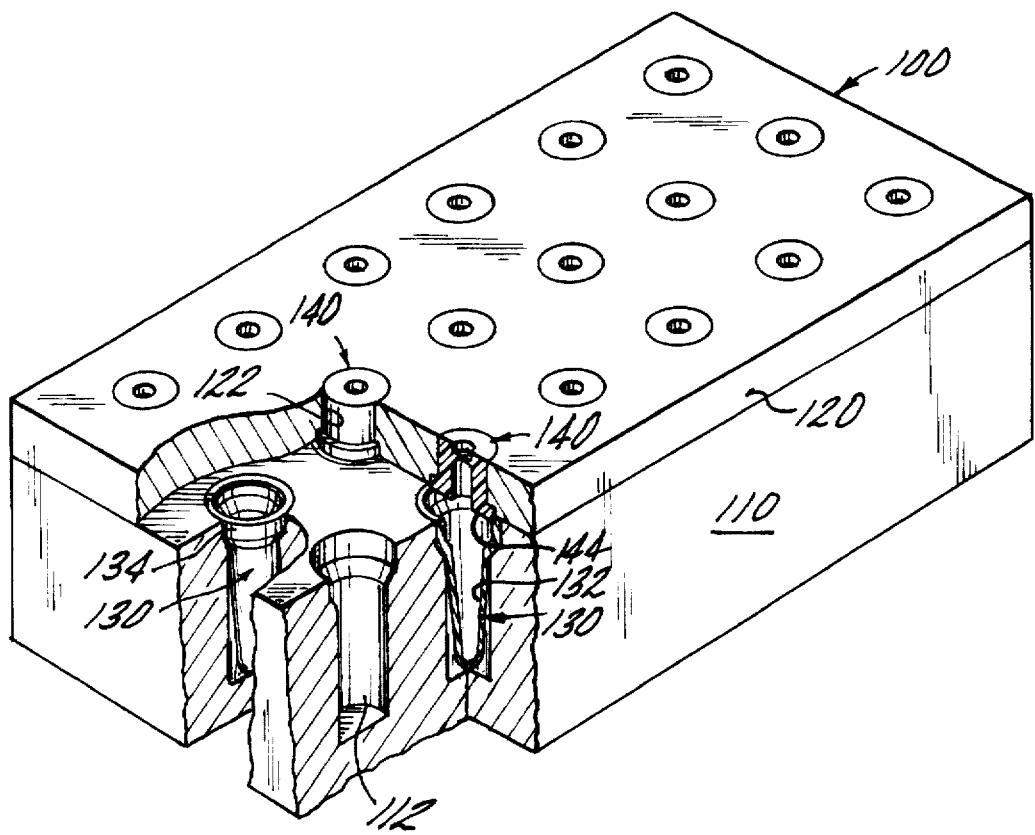
FIG. 4 is a perspective view partially in section of a mold used in the method according to the present invention.
Figures 5, 6:
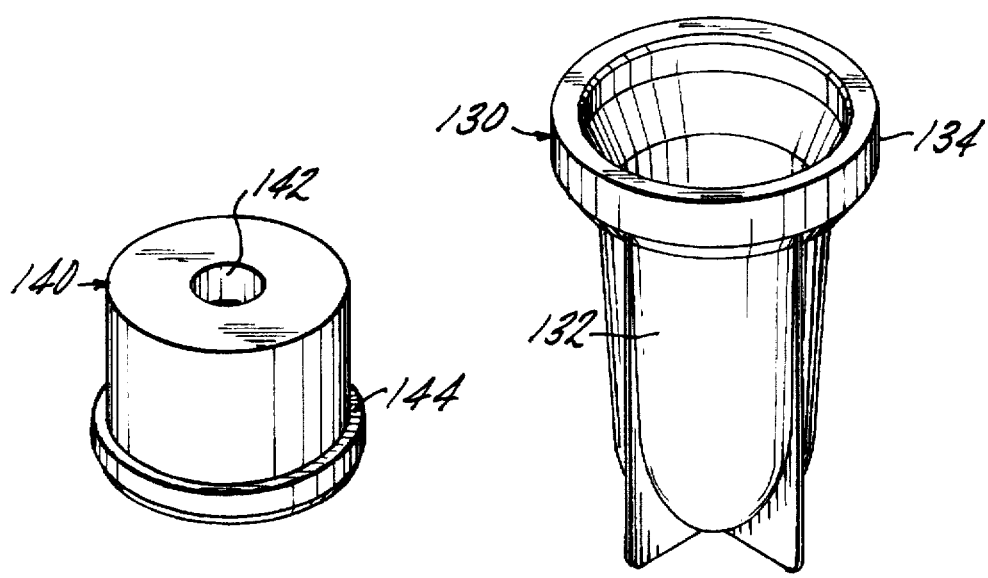
FIG. 5 is a perspective view of a mold insert used in the method according to the present invention.
FIG. 6 is a perspective view of a cap member of the mold used in the method according to the present invention.

A mold suitable for the practice of the method of the present invention is shown in FIGS. 4–6. This mold is based on the mold disclosed in U.S. Pat. No. 5,071,331 to Falco, herein incorporated by reference in its entirety. Thus a two-piece mold 100 is provided, having a bottom 110 and a top 120. Cavities 112 are also provided in a spaced-apart relationship within the bottom 110. Corresponding cavities 122 are provided in top 120. When the mold is closed, cavities 122 will be aligned with cavities 112.

Mold insert 130 includes base portion 132 and a collar 134 which defines a mold cavity. Insert 130 is placed in each mold cavity 112 in bottom 110. Cap member 140 is placed in cavity 122 in the top 120 of the mold 100. Cap member 140 contains opening 142 for accommodation of a porous stem according to the present invention. Cap collar 144 stops the ingress of cap 140 into mold insert 130, and forms a seal with collar 134 of mold insert 130 during foaming. No vent channels need be present in mold insert 130 or cap member 140. Because the porous stem acts as a mold vent during the manufacturing process, foam is prevented from exiting the mold through any mold vents. This reduces waste significantly, as well as manufacturing time.

While preferred embodiments have been shown an described, various modifications and substitutions may be made thereto without departing from the spirit and scope of the invention. Accordingly, it is to be understood that the present invention has been described by way of illustrations and not limitation.

What is claimed is:

1. A hearing protective device comprising a foam and at least one porous component initially discrete from the foam, the porous component being mechanically bonded to the foam by interpenetration of the foam into pores of the porous component.

2. The hearing protective device of claim 1, wherein the porous component comprises at least one polymer containing particles bonded together leaving pores of sufficient size so as to allow controlled penetration of the foam into the pores during manufacture.

3. The hearing protective device of claim 1, wherein the porous component comprises at least one polymer containing small particles bonded together leaving pores of sufficient size so as to allow venting from the mold during manufacture.

4. The hearing protective device of claim 1, wherein the porous component has a pore volume in the range from about 10 percent to about 90 percent of the total volume.

5. The hearing protective device of claim 4, wherein the porous component has a pore volume in the range from about 30 percent to about 60 percent of the total volume.

6. The hearing protective device of claim 1, wherein the porous component is a stem having a handle portion and an embedded portion with a tip.

7. The hearing protective device of claim 6, wherein the stem has variable stiffness, the handle portion of the stem being stiffer than the embedded portion toward the tip.

8. The hearing protective device of claim 7, wherein the variable stiffness results from a variation in the diameter of the cross-section of the stem.

9. The hearing protective device of claim 7, wherein the variable stiffness results from a variation in the density of the stem.

10. The hearing protective device of claim 7, wherein the variable stiffness results from a combination of a variation in the diameter of the cross-section of the stem and a variation in the density of the stem.

11. The hearing protective device of claim 7, wherein the foam is selected from the group consisting of polyurethane, acrylic, acrylic blends, or mixtures thereof.

12. An acoustical foam earplug or semi-aural pod with a stem, wherein the stem has a handle portion and an imbedded portion with a tip, and further wherein the stem has variable stiffness.

13. The foam earplug or semi-aural pod of claim 12, wherein the variable stiffness results from a variation in the diameter of the cross-section of the stem.

14. The foam earplug or semi-aural pod of claim 12, wherein the variable stiffness results from a variation in the material comprising the stem.

15. The foam earplug or semi-aural pod of claim 12, wherein the variable stiffness results from a variation in the density of the material comprising the stem.

16. The foam earplug or semi-aural pod of claim 12, wherein the variable stiffness results from a variation of the hardness of the material comprising the stem.

17. The foam earplug or semi-aural pod of claim 12, wherein the variable stiffness results from a combination of at least two of a variation in the diameter of the cross-section of the stem, a variation in the material comprising the stem, a variation in the density of the material comprising the stem, and a variation in the hardness of the material comprising the stem.

18. A set of acoustical foam earplugs comprising
a porous stem disposed within each earplug, each stem having a handle portion and an embedded portion; and
a flexible cord with two ends, each end of the cord being mechanically attached to each respective handle of the porous stem by interpenetration of the material of the cord into pores of the porous stem.

19. The set of earplugs of claim 18, wherein the porous stem has a variable stiffness.

20. An earmuff comprising
a foam and at least one porous component initially discrete from the foam, the porous component being mechanically bonded to the foam by interpenetration of the foam into pores of the porous component.

21. The earmuff of claim 20, wherein the porous component is a seal plate.

22. A method of making a hearing protective device comprising at least one foam component and at least one porous component initially discrete from the foam, comprising
placing the porous component into a mold;
introducing a foam or foamable mixture into the mold; and
causing the foam to rise and interpenetrate pores in the porous component, thereby forming a mechanical bond between the porous component and the foam.

23. The method of claim 22, wherein the porous component allows venting from the mold.

24. The method of claim 22, wherein the foam or foamable mixture is self-rising.

25. The method of claim 22, wherein the foam is selected from the group consisting of polyurethane, acrylic, acrylic blends, or mixtures thereof.

26. The method of claim 22, wherein the porous component has a pore volume in the range from about 10 percent to about 90 percent of the total volume.

27. The method of claim 26, wherein the porous component has a pore volume in the range from about 30 percent to about 60 percent of the total volume.

28. The method of claim 22, wherein the foam component is an earplug and the porous component is an earplug stem having a handle portion and an embedded portion with a tip.

29. The method of claim 22, wherein the stem has variable stiffness, the handle portion of the stem being stiffer than the embedded portion toward the tip.

30. The method of claim 29, wherein the variable stiffness results from a variation in the diameter of the cross-section of the stem.

31. The method of claim 29, wherein the variable stiffness results from a variation in the density of the stem.

32. The method of claim 29, wherein the variable stiffness results from a combination of a variation in the diameter of the cross-section of the stem and a variation in the density of the stem.

33. The method of claim 29, wherein the variable stiffness results from a combination of at least two of a variation in the diameter of the cross-section of the stem, a variation in the material comprising the stem, a variation in the density of the material comprising the stem, and a variation in the hardness of the material comprising the stem.

34. The method of claim 22, wherein foam component and the porous component are part of an earmuff.

\* \* \* \* \*